United States Patent [19]

van der Puije et al.

[11] Patent Number: 4,762,135
[45] Date of Patent: Aug. 9, 1988

[54] COCHLEA IMPLANT

[76] Inventors: P. D. van der Puije, Lot 13, Concession 2, Rideau Township, Ontario K0A 2T0; Carlos R. Pon, 1535 Alta Vista Drive, Apt. 504, Ottawa, Ontario, K1G 3N9, both of Canada

[21] Appl. No.: 798,337

[22] Filed: Nov. 15, 1985

[30] Foreign Application Priority Data

Aug. 30, 1985 [CA] Canada ................................. 489804

[51] Int. Cl.⁴ .............................................. A61N 1/05
[52] U.S. Cl. ................................................. 128/784
[58] Field of Search ............................... 128/784–786, 128/789, 642

[56] References Cited

U.S. PATENT DOCUMENTS

| | | | |
|---|---|---|---|
| 3,752,929 | 8/1973 | Fletcher | 179/1 SA |
| 4,261,372 | 4/1981 | Hansen et al. | 128/784 |
| 4,284,085 | 8/1981 | Hansen et al. | 128/784 |
| 4,284,856 | 8/1981 | Hochmair et al. | 179/107 |
| 4,461,304 | 7/1984 | Kuperstein | 128/642 |
| 4,462,401 | 7/1984 | Burgio | 128/303 |
| 4,462,402 | 7/1984 | Burgio et al. | 128/303 |
| 4,487,210 | 12/1984 | Knudsen et al. | 128/785 |
| 4,516,820 | 5/1985 | Kuzma | 339/48 |

FOREIGN PATENT DOCUMENTS 1115352 12/1981 Canada ................................. 326/17

OTHER PUBLICATIONS

Pochay et al, "A Multichannel Depth Probe..." IEEE Trans on Biomedical Eng., vol. BME-26, No. 4, Apr. 1979, pp. 199–206.
May et al, "A Tantalum-on-Sapphire ... Array"; IEEE Trans on Electron Devices, vol. ED-26, No. 12, Dec. 1979, pp. 1932–1939.
Sonn et al, "A Prototype Flexible Microelectrode...", MED & Biol. Eng., pp. 778–790, Nov. 1974.

Primary Examiner—Lee S. Cohen
Attorney, Agent, or Firm—Stevens, Davis, Miller & Mosher

[57] ABSTRACT

A small diameter rolled up electrode array for implantation in the cochlea is provided herein. The array includes a flexible, biologically-inert planar support member which has been rolled up to a cylindrical shape to have a proximal end and a distal end. A plurality of electrodes is located at predetermined, spaced distances along a portion of the length of the rolled up, cylindrically-shaped support member starting at the proximal end, each of the electrodes comprising an open ended ring almost encircling the support member and a conducting feedline monolithically associated with each electrode, such feedline lying on the outer surface of the rolled up curved outer surface of the rolled up cylindrical support member, and extending from each associated electrode to the distal end thereof. The support member is thus being rolled up into a cylindrical shape to facilitate insertion of the electrode array into the cochlea while minimizing trauma during the insertion procedure.

14 Claims, 1 Drawing Sheet

COCHLEA IMPLANT

BACKGROUND OF THE INVENTION (i) Field of the Invention

This invention relates to a novel cochlea implant electrode and to a procedure for its manufacture, as well as to an article of manufacture for subsequent forming into such novel cochlea implant electrode and for a procedure for its manufacture.

(ii) Description of the Prior Art

The cochlea is a spiral bone in the temporal bone which contains the organ and nerves of hearing by which sound is perceived. At the present time, in various countries of the world, attempts are being made directly to stimulate the auditory nerves in the cochlea so that a person puffering from nerve deafness can "hear".

Electrodes of this kind have been described by Martin Sonn and Wolfgang Feist in an article entitled "A prototype flexible microelectrode array for implant-prosthesis applications" in Medical and Biological Engineering, Nov. 1974, pages 778–790. This prior art electrode is disposed to be inserted through an aperture in a turn of a patient's cochlea, whose internal ear is defective, in order to establish communication substantially in the area of the cochlea containing the acoustic nerves pertaining to that part of the audible spectrum, which is relevant to the intelligibility of speech.

Schindler et al, in "Multielectrode Intracochlear Implants" Arch Otolaryngol, Vol. 103, December 1977, discloses the use of spatial excitation of the cochlear nerve in cats.

Clark and Hallworth, in "A Multiple-electrode Array for Cochlear Implant", J. Laryngol, Otol 90/7, 1976 disclose a ribbon array including a plurality of elongated flat electrodes which are positioned along the length of the cochlea for stimulating the auditory nerve.

Similarly, bundles of thin wires have been employed by the Stanford Auditory prosthesis group by direct placement into the auditory nerve. Furthermore several other cochlea prostheses have been described in the prior art, including some where a connector is provided. See, for example, reports under NIH Contact NO. NO1-NS-7-2367, "Development of Multichannel Electrodes for an Auditory Prosthesis". Connectors for use and implantable medical electronic devices have also been described.

Several methods have been developed electrically to stimulate nerve fibers in the cochlea of a deaf person in a pattern roughly corresponding to longitudinal mechanical waves produced in the environment (which waves are heard as sound by persons with normal hearing) to thus produce the sensation of sound in the deaf person. The details and results of one such method are set forth in a document entitled "Cochlear Implants:. Progress and Perspectives" edited by William F. House and Karen I. Berliner, and which is Supplement 91-Volume 91, March–April 1982, No. 2, Part 3 of the Annals of Otology, Rhinology and Laryngology, publiphed by The Annals Publishing Company, 4949 Forest Park Blvd., St. Louis Mo., 63108, copyright 1982.

Generally such methods involve implanting an internal electromagnetic coil connected by leads to active and ground electrodes under the skin covering the person's skull and positioning the electrodes at predetermined locations in or adjacent the cochlea. An externally worn adjustable transducer is then used to produce electrical signals in response to longitudinal mechanical waves produced in the environment and received via a microphone on the device, and to couple those electrical signals to an external electromagnetic coil positioned on the outside of the skin opposite the coil under the skin. Electrical signals corresponding to those produced by the transducer are produced in the internal coil by magnetic coupling between the coils, and those signals stimulate the cochlea via the electrodes. While the signals do not produce the same sound sensations from the mechanical waves that the waves produce via the normal human ear, they do produce a range of sound sensations that, with training, can be used by the person to help identify the source of the waves and in many cases to help the person understand human speech.

Implanting the coil with its leads and electrodes under the skin covering the person's head generally comprises (1) exposing the outer surface of the person's temporal bone behind the ear, which is typically done by cutting an arcuate slit in the skin, muscle, and other tissue overlaying that bone, separating, and laying back the flap thus produced; (2) making an opening in the temporal bone through the mastoid and facial recess portions of the temporal bone between the outer surface of the temporal bone and the round window in the cochlea; (3) forming a recess for the coil via a surgical drilling device in the exposed squamous portion of the temporal bone; (4) locating and attaching the internal coil in the recess; (5) positioning the ground electrode in the eustachian tube or some other location such as the opening in the mastoid or under the temporalis muscle; (6) positioning the lead terminating at the active electrode through the surgically prepared opening with the electrode at a predetermined position relative to the cochlea (e.g., which position may be at the outside surface of the round window of the cochlea or inside the cochlea with the lead passing through the round window); (7) anchoring the leads in place through the use of an acceptable adhesive or by packing tissues from the head around them in the opening; and (8) then replacing the flap of skin, muscle, and other tissues by suturing it in place over the coil and opening, and allowing the slit that formed the flap to heal.

Other similar methods have involved the use of a plurality of leads which terminate at spaced active electrodes adapted to be inserted into the cochlea through the round window under the theory that selective activation of the electrodes may selectively stimulate different nerves in the cochlea and result in better sound discrimination by the person.

As noted above, in its usual form, a cochlear prosthesis consists of two parts implanted into the skull of the patient. The first part is an "electronics" package which is implanted in the mastoid bone behind the ear. The second part consists of an electrode assembly which is inserted into the cochlea in order to apply electrical stimulation to auditory nerve fibers. The electrode array or assembly must be electrically connected to the electronics package. In addition, an internally-worn transmitter/receiver device is used to transfer both information and power to the implanted unit, and may receive information telemetered back from the implant.

In order to stimulate the nerves it is necessary to insert at least one electrode in the cochlea and this insertion can be done through the round window or by drilling a hole into the cochlea. It is generally believed to be desirable to stimulate the nerves at various spaced positions along the length of the cochlea as the different frequencies perceived by a person with normal hearing are developed by stimulation of various nerves along the cochlea. The locations of these nerves have a relationship with the frequency perceived and, thus, it is essential to use an electrode array with electrodes at the required spaced positions and which, in itself, can be passed along the spiral of the cochlea.

As noted hereinabove, there have been previous forms of electrode arrays proposed, one of which was a stranded wire array in which electrodes were formed by the termination of the wires at various positions along the length of the array, the terminated wire being stripped and spirally wound around the other wires of the array. Such stranded electrodes provided the necessary electronic properties and, to a greater or lesser extent, the required mechanical properties. These electrodes were, however, found to be unsatisfactory as it was difficult to form them with a smooth outer surface and on insertion they tended to cause trauma. Sputtered arrays have also been proposed but it has been difficult and expensive to attempt to manufacture such arrays as they needed application of a very advanced form of technology.

Many problems have arisen in the implanting of such electrodes in the cochlea, and because of such problems numerous situations have been proposed. It was found, for example, that such an electrode had to be introduced into about nearly two turns of cochlea. It has appeared, however, that a satisfactory result was not attained, for while it was possible to bring the patient to such a condition that the patient could interpret electrical signals supplied through the electrode as being sound, such sound was not interpreted as being intelligible speech. This fact was said to be due to damaging the patient's acoustic nerves during the insertion of the electrode into the cochlea.

The invention in U.S. Pat. 4,261,372 patented Apr. 14, 1981 by C. C. Hansen et al was based on the acknowledgement that the entire area of cochlea which was relevant to speech could not be contacted collectively, because an electrode having a sufficient extension for this purpose would act unavoidably as a chisel, which during the introduction would gouge into cochlea and in this way damage the interior walls of the cochlea and possibly the acoustic nerves too.

That patentee alleged to provide such an electrode in which the draw-backs of the prior art electrode were obviated by providing an electrode in the form of a foil-like flexible, electrically insulating support member having nerve electrodes supported thereupon for implantation into the cochlea. The electrode established electrical communication to the acoustic nerves of the human ear, substantially in the area of the cochlea containing the auditory nerves pertaining to that part of the audible spectrum, which was relevant to the intelligibility of speech. The electrode had two prongs and a shank, each prong having a length which corresponds to the length of the turn in the cochlea into which it is to be inserted during implantation and hence the two prongs are of different lengths. Further, each prong terminated in a bevelled pilot guiding member which guided each prong through its respective turn in the cochlea, thereby to reduce damage to the auditory nerves. During implanation each prong passes through only a single turn of the cochlea and was prevented from gouging into the walls of the cochlea due to the provision of the bevelled guiding member. The guiding member could be provided as a drop-shaped member secured to the end of each prong or by forming an eyelet in the distal ends of the prongs.

These same patentees provided a further alleged improvement in the prior art cochlea electrode. In U.S. Pat. 4,284,085, patented Aug. 18, 1981 these patentees provided an electrode for implanation into the cochlea. Their invention provided an electrode, which had two conditions of curvature, the one of which was temporary and corresponded to the curvature in the middle of the particular turn of the cochlea and the other one of which was permanent and corresponded to the first position of the electrode in the cochlea in which position it obtains an optimum contact to the acoustic nerves. The electrode of that invention further contained elements for changing the condition of curvature from the temporary one to the permanent one when the electrode had been inserted into the cochlea. The permanent condition of curvature was constituted by the natural condition of curvature of the electrode, whereas the temporary condition of curvature was established by means of a detachable or loosenable connection, which, until it was detached or loosened, maintained the temporary condition of curvature.

Other patentees provided what were said to be further improvements on such electrodes. Thus, U.S. Pat. No. 3,752,929 disclosed the use of an electrode including a pair of elongated conductors for implanting in the cochlea. In addition, in U.S. Pat. No. 4,284,856, a multichannel auditory stimulation system was disclosed wherein selected cochlea excitation was achieved by using a multielectrode prosthetic device which was inserted in the scala tympani of the cochlea. Different tones could be perceived by the patient through selective excitation of the cochlea with the multi-electrode prosthetic device.

In respect of such cochea implants, it was noted that another problem was present, namely that of properly positioning the electrodes with respect to the cochlea and holding the electrodes in that desired position. Experience had shown that positioning of the active electrode often disrupted the delicate soft tissues of the cochlea (e.g., the basilar membrane or spiral ligament), and that a positioned electrode was sometimes inadvertently moved from the desired position during the operation. Also, it was found to be necessary sometimes to replace the internal coil during a revision surgery which was done by again making an arcuate incision and folding back a flap of skin, muscle and other tissues from over the internal coil, cutting the lead or leads connected to the internal coil, reconnecting a new internal coil, and saturing the flap in place over the new internal coil. Inadvertent movement of the electrodes occurred during such severing and reconnecting of the leads which could result in damage to the cochlea or an improper new position for the electrodes. Such movement occured because the anchor tissues packed around the leads did not attach firmly to the lead, and because of the slight force necessary to move the leads.

Solutions to such problems were said to be provided in U.S. Pat. No. 4,462,401 patented July 31, 1984 by P. A. Burgio, in U.S. Pat. No. 4,462,402 patented July 31, 1984 by P. A. Burgio et al, and in U.S. Pat. No. 4,487,210 patented Dec. 11, 1984 by W. L. Knudsen et al. In each of these patents, a method was provided for implanting electrodes in or around a human cochlea that involved inserting one end of an anchor in the temperal bone, and functionally engaging a lead to the electrode with the anchor. Numerous anchor embodiments were described together with tools for inserting some of the anchors.

Another major problem with a cochlea prosthesis, was that entire replacement of the device was probably not feasible with present-day technology. The electrode assembly, once it has been implanted into the cochlea, probably could not be explanted without damage to the cochlea itself. The electrode assembly must thus be designed to have a long life (in the order of fifty years, or the expected life of the patient). However, it may be necessary or desirable to replace the electronics package, for example, due to a circuit failure, or to substitute a compatible assembly of more advanced design at some time in the future. Thus, permanent connections between the electronics package and the electrodes are not appropriate.

In a cochlea prosthesis, the connection problem is severe. Firstly, many connections were required between the electronics package and the electrodes in a cochlear prosthesis. Secondly, because of the confined space in the skull where the cochlear prosthesis was required to fit, the space constraints were severe. In addition, it was desirable for surgical convenience and safety to be able to make all connections between the electronics package and the electrodes simultaneously, with one procedure. Furthermore, the reconnection process must take place in an environment where fluid ingress cannot be prevented; since the electrode assembly remains permanently in the skull, each re-connection of the electrodes to a new electronics package must take place inside the patient's head.

U.S. Pat. No. 4,516,820 patented May 14, 1985 by J. Kuzma was said to solve some of the disadvantages of the above-noted prior art connector techniques. That patentee provided a cochlea prosthetic package having an electronics part and an electrode part. The two parts had ceramic plates with aligned, hermetically-sealed hollow-pin feedthroughs therein. The parts were connected by a silicone-elastic sheet having individual metal foil pieces extending therethrough, each piece of metal foil having its two ends bent over to lie flush against respective faces of the sheet. The metal foil ends contacted the feedthroughs to establish the electrical connections.

Another problem was to provide a sufficiently flexible electrode array. This problem was said to be solved by G. M. Clark et al in Canadian Pat. No. 1,115,352 issued Dec. 29, 1981. That patent provided an electrode array comprising a flexible, biologically-inert tube, a number of eletrodes conducting bands located at predetermined spaced distances along portion of the length of the tube, the electrodes lying, generally, within the diameter of the tube and a conducting wire associated with each electrode and passing to the interior of the tube through a slot, aperture or the like in the tube at a position beneath the associated electrode to which the wire is connected and along the length of the tube to one end thereof. If required, the tube could be filled completely or in part with a material with appropriate mechanical properties. Preferably each electrode was formed from a thin film of a biologically inert metal, e.g. platinum, and the tube could be of a biologically clean grade silicone rubber.

SUMMARY OF THE INVENTION (i) Aims of the Invention

The present invention has for its main aim the provision of an improved cochlea implant electrode. It has been noted that, in spite of these many alleged improvements in cochlea implants, a major problem still existed, namely in the manufacture of such an electrode. Such electrodes have a multiplicity of electrode surfaces and connecting leads, all of which must fit within a cochlea having a diameter of the order of 1 mm. It is clear that the delicate, hand-made cochlea implant electrodes cannot provide a commercial solution to the adequate supply thereof for widespread use.

It is therefore one main object of this invention to provide an easily mass-produced electrode array which is sufficiently flexible to be able to be passed around the spiral of the cochlea while being sufficiently stiff to be fed and which has electrodes spaced at predetermined spacings, which electrodes are adapted to contact the nerve endings in the cochlea.

(ii) Statements of Invention

By this invention, a small diameter electrode array is provided for implantation in the cochlea, comprising a flexible, biologically-inert, planar support member rolled up to a cylinderical shape having a proximal end and a distal end; a plurality of electrodes located at predetermined, spaced distances along a portion of the length of the rolled-up, cylindrically-shaped support member starring at the proximal end thereof, each of the electrodes comprising an open-ended ring almost encircling the support member, and a conducting feedline monlithically associated with each electrode, such feedline lying on the outer surface of the rolled-up support member, and extending from each associated electrode to the distal end thereof; the support member thus being rolled-up to facilitate insertion of the electrode array into the cochlea while minimizing trauma during the insertion procedure.

(iii) Other Features of the Invention

It is preferred that each of the electrodes and its associated monolithic conducting feedline be formed of metal, e.g. of platinum, rhodium, tungsten or molybdenum, and that each monolithic conducting feedline be intergral with its associated electrode. It is also preferred that the support member be formed of a synthetic plastics material, e.g., a polyimide, a polytetrafluoreothylene (known by the trade mark TEFLON) or that known by the trade mark PARALENE. The electrode array may be hollow, or it may be filled with a flexible resilient material, e.g., a silicone rubber. The maximum diameter of the electrode array is preferably 1 mm.

The electrode array is specially adapted to be formed from a planar array including a plurality of spaced-apart electrodes, each electrode comprising a rectangular piece of electrically-conducting material and a monolithically associated feedline, the electrodes being supported on a flexible, biologically-inert planar base member.

In such array the electrodes are formed of metal, e.g., platinum, rhodium, tungsten or molybdenumand that the monolithic feedline be intergral with each associated electrode. The planar base member is preferably a synthetic plastics material, e.g., a polyimide, TEFLON or PARALENE.

BRIEF DESCRIPTION OF THE DRAWINGS

In the accompanying drawings.

Figure 1:
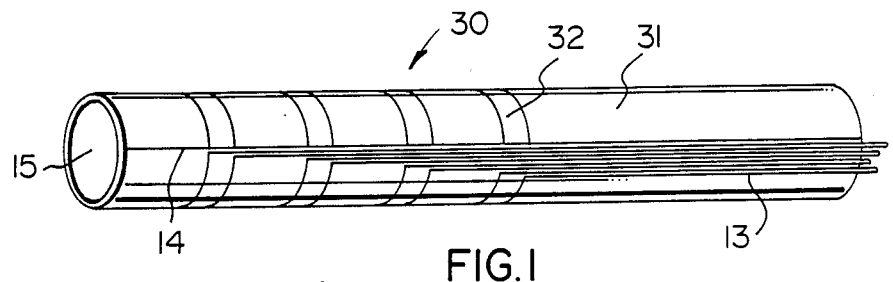
FIG. 1 is a perspective view of an electrode array for implantation into the cochlea, according to one embodiment of the invention.
Figure 2:
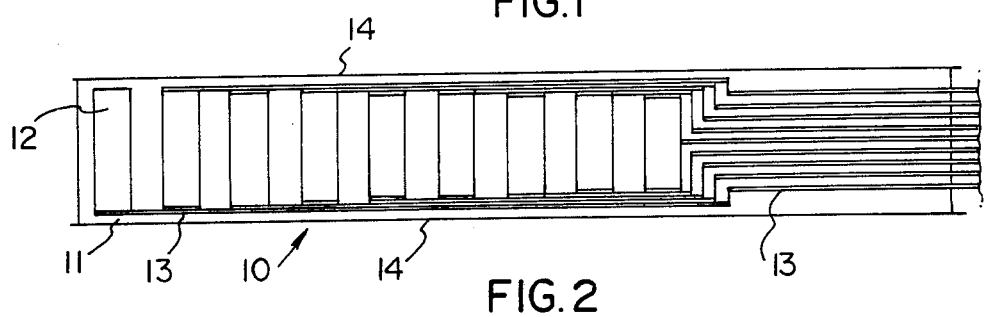
FIG. 2 is a top plan view of a supported planar array of electrodes for conversion into the embodiment of electrode array of FIG. 1.

DESCRIPTION OF PREFERRED EMBODIMENTS (i) Description of Manufacturing Procedure The first step in the production of the cochlea implant electrode array shown in FIG. 1 is the preparation of a planar electrode array as in FIG. 2. This is done by means of standard procedures which are well known in the semi-conductor industry. The manufacturing procedure is thus easy to automate. The mask which determines the configuration of the conducting metal, e.g. platinum pads and feedlines is computer generated. It is therefore accurate and can be changed without difficulty.

One particular procedure which has been used to fabricate the planar array, which is an adaptation of standard procedure in the semi-conductor industry, is as follows:

1. Clean silicon slice using the standard RCA technology by the following steps:
   (a) 10 min. $NH_4OH + H_2O + H_2O_2$ at 80° C. (400:80:80);
   (b) 10 min. rinse with $H_2O$;
   (c) 10 min. $HCL = H_2O + H_2O_2$ at 80° C. (420:70:70);
   (d) 10 min. rinse with $H_2O$;
   (e) 2 min. 10% (by weight) HF;
   (f) 10 min. rinse with $H_2O$; and
   (g) blow dry nitrogen.
2. Evaporate aluminum on top of the slice to a thickness of 10,000 A.
3. Spin polyimide solution in a suitable thinner, e,g. that known by the Trade Mark T9035 by Du Pont with a spin speed of 800 RPM for 30 sec; thickness of 13 um.
4. Full cure of the polyimide film is achieved at the following temperatures and times:
   50° C.—hr.
   100° C.—1 hr.
   120° C.—1 hr.
   140° C.—20 min.
   175° C.—20 min.
   190° C.—20 min.
   215° C.—20 min.
   235° C.—20 min.
   260° C.—20 min.
   280° C.—20 min.
   300° C.—1 hr.
   350° C.—30 min
5. Repeat steps 3 and 4, two more times to give a thickness of 40 um. total.
6. Sputter titanium to a thickness of approx. 400 A by the following procedure;
   (a) pre-sputter the target at 100 W for 3 min. (tunning input: 5.25, and load tunning: 13.3)
   (b) sputter-etch the polyimide surface at 80 W for 5 min. (tunning input: 6.0, load tunning: 10.8)
   (c) sputter titanium on the clean polyimide surface of 100 W for 5.25, load tunning: 13.4)
7. Sputter platinum to a thickness of approx. 3000 A by the following procedure:
   (a) pre-sputter the target at 100 W for 3 min. (tunning input: 5.25, and load tunning: 13.5);
   (b) sputter-etch the titanium oxide at 80 W for 2.5 min.(tunning input: 6.0, load tunning: 10.75);
   (c) sputter platinum on the titanium surface at 100 W for 30 min. (tunning input: 5.25, load tunning: 13.5;) note: argon pressure must remain at $8 \times 10^{-3}$ Torr for steps 6 and 7, and vacuum pressure should not be lower than $1.2 \times 10^{-6}$ Torr.
8. Spin positive photoresist at 2000 RPM for 45 sec. on the slice.
9. Pre-exposure bake at 70° C. for 100 min.
10. Use electrode mask to define electrodes array and expose in ultraviolet light for 6 sec.
11. Develop slice in a suitable developer solution for 1 min., followed by 1 min rinse in distilled water. One example is that known by the Trade Mark LSI known for developing a positive photoresist, diluted 50:50 with distilled water.
12. Post-bake the slice of 80° C. for 90 min.
13. Sputter etch the platinum and titanium at 80 W for 35 min.
14. Strip the photoresist using actone swabbing.
15. Inspect under the microscope to see if there is any photoresist left in the edges of the electrodes.
16. Bake at 50° C., 80° C., 100° C., and 120° C. for 20 min at each step.
17. Sputter etch at 80 W for 5 min. to remove any photoresist left.
18. Spin polyimide solution at 1500 RPM for 30 sec. This gives a thickness of 10 um.
19. Short cure cycle as follows:
    (a) 50° C. for 20 min.;
    (b) 100° C. for 20 min.; and
    (c) 120° C. for 30 min.
20. Spin positive photoresist at 2000 RPM for 45 sec. on the slice.
21. Pre-exposure bake at 70° C. for 100 min.
22. Use electrode mask to define the contact windows and vias opening. Expose in ultraviolet light for 6.5 sec.
23. Develop the slice in LSI:distilled water (50:50) solution for 25 sec. and then rinse in distilled water for 1 min. At this time the polyimide is also dissolved because it is not completely cured. This permits one to open the vias and contact pads through the platinum.
24. Strip the photoresist carefully with warm acetone at 50° C.
25. Complete the cure cycle as follows:
    (a) 50° C. for 1 hr.;
    (b) 100° C. for 1 hr.;
    (c) 120° C. for 1 hr.;
    (d) 140° C. for 20 min.;
    (e) 160° C. for 20 min.; and
    (f) 180° C. for 2 hr.
26. Cut the slice on the edges to make the solution of HC1: D distilled water I (50:50) dissolve the aluminum and lift the electrodes sandwich arrays.
27. Cut the electrodes with a special punch.

Figure 3:
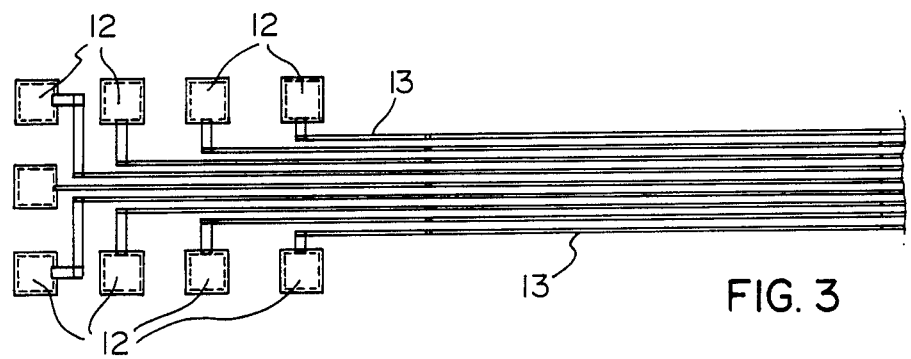
FIG. 3 is a view of the end of the electrode array where it is connected to an electronic stimulator (not shown)

(ii) Description of FIGS. 2 and 3

Referring now to FIGS. 2 and 3, the planar electrode 10 formed as described above includes a base 11 of a synthetic plastics material, e.g. a polyimide, a plurality of spaced-apart, rectangular electrodes 12, e.g. of platinum, and a monolithically-associated feedline 13 for each electrode 12.

The next step in the manufacture of the cochlea implant electrode is to roll the planar rectangular structure 10 so formed into a long, narrow cylinder with the rectangular platinum pads on the outside.

Figure 4:
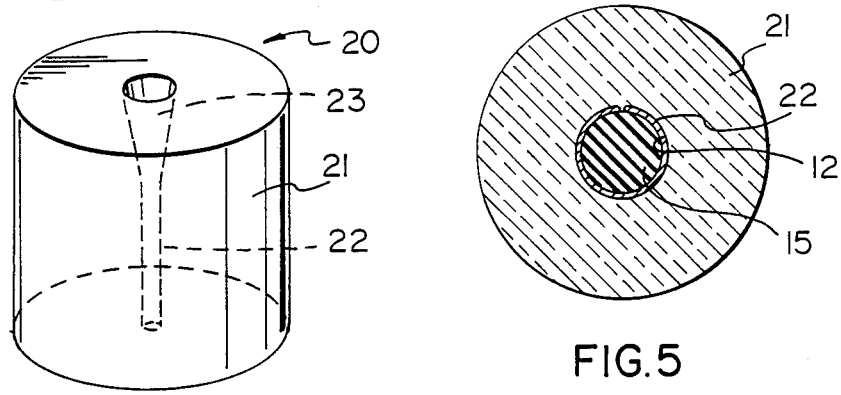
FIG. 4 is a perspective view of a jig designed to convert a planar electrode array into a curved electrode array.
Figure 5:
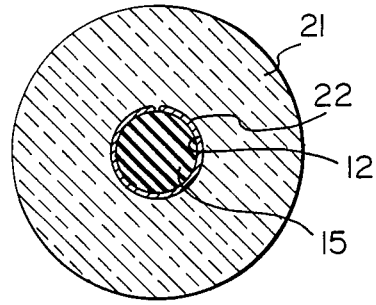
FIG. 5 is a cross-section of an electrode array within the jig of FIG. 4 and adapted to provide the electrode array of FIG. 1.

(iii) Description of FIGS. 4 and 5

In order to roll the planar electrode, a jig 20 made out of a block of material e.g. the polymethacrylate plastic known by the Trade Mark PLEXIGLASS as shown in FIGS. 4 and 5 is used. This block 21 includes a hole 22 of 1 mm diameter drilled through the centre of the cylindrical piece of PLEXIGLASS 21 with a funnel-shaped lead-in 23 provided. The planar electrode is carefully pushed in at the funnelled end so that the electrode curves around the inside of the 1 mm. hole. The width of the planar electrode is made such that the lateral edges 14 of the eletrode meet, i.e. by being $\lambda$mm wide. Medical grade silicone rubber 15 is injected into cylindrical cavity formed by the rolled, planar electrode 10. The silicone rubber is cured and the cochlea implant electrode 20 is then withdrawn. The cochlea implant electrode 30 retains its cylindrical structure with the rectangular platinum strips 12 taking the form of cylindrical bands 32 on the outside, of the polyimide cylinder 31 as shown in FIG. 1.

(iv) Description of FIG. 1

In addition, as seen in FIG. 1, there are monolithically associated feedlines 13 along the outer surface of the cylinder 31, with a seam 14 separating the rolled ends of the electrodes 12, to provide the almost-ring-like electrodes 32. The almost-ring-like electrodes 32 start at a proximal end of the rolled-up electrode 30 and are longitudinally spaced therealong to extend towards a distal end thereof. The monolithically-associated feddlines 13, each of which is preferably integral with its associated electrode 32, extend longitudinally along the outer curved surface of the cylinder 31 to the distal end thereof.

OPERATION OF PREFERRED EMBODIMENT

It will be seen that there are a number of additional advantages of the various aspects of this invention, namely:

All the steps in the manufacturing process are standard processes well known in the semi-conductor industry, and hence easy to automate. The process of converting the flat electrode into a cylinder is simple and can easily be automated.

The large surface area of the electrode pads keeps the electrode impedance low so that limiting factor of current density will not be a problem. The electrode surface is smooth and should be easy to insert in the cochlea.

The materials and processing steps in the manufacture lead to an electrode that is non-toxic to tissue and at the same time is inert to biological fluids and tissue.

Because the electrode pads are rings, it is not necessary for the surgeon to maintain any particular orientation when inserting the electrode in the cochlea.

By adjusting the thickness of the polyimide layer, the flexibility/stiffness properties of the cochlea electrode can be optimized. The structure is compatible with the use of "memory" alloys e.g., that known by the Trade Mark NITINOL which will improve the ease of insertion into the cochlea.

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalent of the following claims.

What we claim is:

1. A small diameter, rolled-up, electrode array for implantation in the cochlea, comprising:
    a flexible, biological-inert, planar support member rolled-up to a generally cylindrical shape, and having a proximal end and a distal end;
    a plurality of electrodes located at predetermined, spaced distances along a portion of the length of said rolled-up, cylindrically-shaped support member, each of said electrodes comprising an open-ended ring almost encircling said support member, and a conducting feedline monolithically associated with each electrode, lying on the outer curved surface of said rolled-up support member, and extending from each associated electrode to said distal end;
    said planar support member being of sufficient flexibility to be rolled-up into a cylindrical shape to facilitate insertion of said electrode array into the cochlea while minimizing trauma during the insertion period.

2. The electrode array of claim 1 wherein each of said electrodes and its associated monolithic conducting feedline is formed of metal.

3. The electrode array of claim 2 wherein said metal is platinum, rhodium, tungsten, or molybdenum.

4. The electrode array of claim 1 wherein said support member is formed of a synthetic plastics material.

5. The electrode array of claim 4 wherein said synthetic plastics material is a polyimide, a polytetrafluoroethylene or PARALENE.

6. The electrode array of claim 1 wherein a formed core of said rolled-up support member is hollow.

7. The electrode array of claim 6 wherein said hollow core of said rolled-up support member is filled with a flexible resilient material.

8. The electrode array of claim 7 wherein said flexible resilient material is silicone rubber.

9. The electrode array of claim 1 wherein each electrode comprises a rectangular piece of electrically-conducting material and an intergral feedline, each of said electrodes being supported on the curved surface of said flexible, biologically-inert rolled-up planar support member.

10. The electrode array of claim 9 wherein said electrodes are formed of a metal.

11. The electrode array of claim 10 wherein said metal is platinum, rhodium, tungsten, or molybdenum.

12. The electrode array of claim 11 wherein said planar support member has a maximum width of $\pi$mm to provide a rolled-up cylinder having a maximum diameter of 1 mm.

13. The electrode array of claim 9 wherein said planar support member is a synthetic plastics material.

14. The electrode array of claim 13 wherein said synthetic plastics material is a polyimide, a polytetrafluorethylene or PARALENE.

* * * * *